United States Patent
Kim et al.

(10) Patent No.: US 11,059,927 B2
(45) Date of Patent: Jul. 13, 2021

(54) MODIFIED MONOMER, MODIFIED POLYMER INCLUDING THE SAME, AND METHODS OF PREPARING THE SAME

(71) Applicant: LG Chem, Ltd., Seoul (KR)

(72) Inventors: Min Soo Kim, Daejeon (KR); Won Mun Choi, Daejeon (KR); Dae June Joe, Daejeon (KR)

(73) Assignee: LG Chem, Ltd.

( * ) Notice: Subject to any disclaimer, the term of this patent is extended or adjusted under 35 U.S.C. 154(b) by 593 days.

(21) Appl. No.: 15/753,652

(22) PCT Filed: Dec. 1, 2016

(86) PCT No.: PCT/KR2016/014065
§ 371 (c)(1),
(2) Date: Feb. 20, 2018

(87) PCT Pub. No.: WO2017/105013
PCT Pub. Date: Jun. 22, 2017

(65) Prior Publication Data
US 2018/0244819 A1 Aug. 30, 2018

(30) Foreign Application Priority Data

Dec. 18, 2015 (KR) .................. 10-2015-0181690
Oct. 31, 2016 (KR) .................. 10-2016-0143544

(51) Int. Cl.
| | | |
|---|---|---|
| *C08F 236/06* | (2006.01) | |
| *C07C 43/215* | (2006.01) | |
| *C07C 41/09* | (2006.01) | |
| *C08F 112/14* | (2006.01) | |
| *C08F 236/10* | (2006.01) | |
| *C08F 212/08* | (2006.01) | |

(52) U.S. Cl.
CPC ............ *C08F 236/06* (2013.01); *C07C 41/09* (2013.01); *C07C 43/215* (2013.01); *C08F 112/14* (2013.01); *C08F 212/08* (2013.01); *C08F 236/10* (2013.01)

(58) Field of Classification Search
CPC .... C08F 236/06; C08F 112/14; C08F 212/08; C08F 236/10; C07C 41/09; C07C 43/215
USPC ......................................................... 526/313
See application file for complete search history.

(56) References Cited

U.S. PATENT DOCUMENTS

| | | |
|---|---|---|
| 3,931,107 A | 1/1976 | Trepka |
| 4,882,243 A | 11/1989 | Skotheim et al. |
| 5,468,589 A | 11/1995 | Urano et al. |
| 2006/0269473 A1 | 11/2006 | Kung et al. |
| 2009/0203843 A1* | 8/2009 | Fukuoka .......... C08C 19/25 525/105 |
| 2014/0187723 A1 | 7/2014 | Hsieh et al. |
| 2014/0206793 A1 | 7/2014 | Okabe et al. |
| 2016/0208024 A1 | 7/2016 | Kim et al. |

FOREIGN PATENT DOCUMENTS

| | | |
|---|---|---|
| CN | 101495522 A | 7/2009 |
| CN | 103764746 A | 4/2014 |
| EP | 0520642 A1 | 12/1992 |
| EP | 2868696 A1 | 5/2015 |
| JP | H02212559 A | 8/1990 |
| JP | H05249682 A | 9/1993 |
| JP | 07228686 A * | 8/1995 |
| JP | H07228686 A | 8/1995 |
| JP | 2008524243 A | 7/2008 |
| JP | 2014129514 A | 7/2014 |
| KR | 101022563 B1 | 3/2011 |
| WO | 2008013090 A1 | 1/2008 |
| WO | 2015056994 A1 | 4/2015 |

OTHER PUBLICATIONS

Sinta et al. "Cation and Anion Binding Properties of Poly(vinylbenzoglymes)", Macromolecules, 1980, vol. 13, p. 339-345. (Year: 1980).*
Hallensleben et al. "Polystyrenes with oligo(ethylene oxide) side chains as ionic conducting matrices", Polymer Bulletin, vol. 37, p. 765-770, 1996. (Year: 1996).*
McCairn et al. "A Platform for Both Solid-Phase Peptide Nucleic Acid Oligomer Synthesis and Subsequent in Situ Detection and Quantification of Nucleic Acid Sequence", J. Combinatorial Chemistry, 2006, vol. 8, p. 639-642. (Year: 2006).*
Search report from International Application No. PCT/KR2016/014065, dated Mar. 10, 2017.
Hallensleben, M. L., et al., "Poly(styrene)s with Oligo(ethylene oxide) Side Chains as Ionic Conducting Matrices." Polymer Bulletin, vol. 37, Accepted Aug. 15, 1996, pp. 765-770.
Sinta, Roger, et al., "Cation and Anion Binding Properties of Poly(vinylbenzoglymes)." Macromolecules (1980), vol. 13, pp. 339-345.
Mccairn, Mark C., et al., "A Platform for Both Solid-Phase Peptide Nucleic Acid Oligomer Synthesis and Subsquent in Situ Detection and Quantification of Nucleic Acid Sequences." Journal of Combinatorial Chemistry, vol. 8, pp. 639-642.
Extended Search Report including Written Opinion for Application No. EP16875955.3 dated Nov. 9, 2018.
Fengjun Hua et al: "Temperature-induced phase-transitions of methoxyoligo(oxyethylene) styrene-based block copolymers in aqueous solution", Soft Matter, Jan. 1, 2013, vol. 9, No. 37, p. 8897.

(Continued)

*Primary Examiner* — Ling Siu Choi
*Assistant Examiner* — Ronald Grinsted
(74) *Attorney, Agent, or Firm* — Lerner, David, Littenberg, Krumholz & Mentlik, LLP

(57) ABSTRACT

The present invention relates to a substituted styrene-based compound represented by Formula 1 (refer to the specification and the scope of the claims), a method of preparing the styrene-based compound, a modified polymer including a functional group derived from the substituted styrene-based compound, a method of preparing the modified polymer, a rubber composition including the modified polymer, and a molded article manufactured from the rubber composition.

4 Claims, No Drawings

(56) References Cited

OTHER PUBLICATIONS

Alesso, et al., "Improving Resins for Solid Phase Synthesis: Incorporation of 1-[2-(2-Methoxyethoxy)Ethoxy]-4-Vinyl-Benzene", Tetrahedron, vol. 59, No. 36, Sep. 2003, pp. 7163-7169.
Chinese Search Report for Application No. 201680053009.6 dated Dec. 20, 2019, 4 pages.

* cited by examiner

MODIFIED MONOMER, MODIFIED POLYMER INCLUDING THE SAME, AND METHODS OF PREPARING THE SAME

CROSS-REFERENCE TO RELATED APPLICATION

The present application is a national phase entry under 35 U.S.C. § 371 of International Application No. PCT/KR2016/014065 filed Dec. 1, 2016, which claims priority from Korean Patent Application Nos. 10-2015-0181690, filed on Dec. 18, 2015, and 10-2016-0143544, filed on Oct. 31, 2016, the disclosures of which are incorporated herein by reference in its entirety.

CROSS-REFERENCE TO RELATED APPLICATION

This application claims priority to and the benefit of Korean Patent Application Nos. 10-2015-0181690, filed on Dec. 18, 2015, and 10-2016-0143544, filed on Oct. 31, 2016, the disclosures of which are incorporated herein by reference in its entirety.

TECHNICAL FIELD

The present invention relates to a styrene-based compound useful for polymer modification, a method of preparing the compound, a modified polymer including a functional group derived from the styrene-based compound, a method of preparing the modified polymer, a rubber composition including the modified polymer, and a molded article manufactured from the rubber composition.

BACKGROUND ART

According to the recent requirement for automobiles to be fuel-efficient, polymers, which have low rolling resistance, high wear resistance, excellent tensile characteristics, and handling stability represented as wet skid resistance, are required as a rubber material for tires.

To reduce the rolling resistance of tires, there is a method of decreasing the hysteresis loss of vulcanized rubber. As evaluation standards of such vulcanized rubber, repulsive elasticity at 50° C. to 80° C., tan δ, Goodrich heating, and the like are used. That is, rubber materials with high repulsive elasticity at the above-described temperature range or low tan δ and Goodrich heating are preferably used.

As rubber materials having a low hysteresis loss, natural rubber, polyisoprene rubber, polybutadiene rubber, and the like are known, but these materials have low wet skid resistance. Thus, conjugated diene-based (co)polymers such as styrene-butadiene rubber (hereinafter, referred to as SBR) or butadiene rubber (hereinafter, referred to as BR), prepared by emulsion polymerization or solution polymerization, have recently been used as rubber for tires. Among these, the biggest advantage of solution polymerization over emulsion polymerization is that the contents of a vinyl structure and styrene, which determine physical properties of rubber, may be arbitrarily adjusted, and molecular weights, physical properties, and the like may be adjusted by coupling, modification, or the like. Thus, SBR rubber prepared by solution polymerization through which it is easy to structurally change the finally prepared SBR or BR, movement of chain terminals may be decreased by binding or modifying the chain terminals, and the SBR rubber may have increased binding strength with a filler such as silica, carbon black, or the like is widely being used as a rubber material for tires.

When such solution-polymerized SBR is used as a rubber material for tires, a glass transition temperature of rubber may be increased by increasing a vinyl content in the SBR, and thus physical characteristics required for tires, such as driving resistance and braking force, may be adjusted, and fuel consumption may also be reduced by appropriately adjusting the glass transition temperature.

The solution-polymerized SBR is prepared using an anionic polymerization initiator, and chain terminals of the formed polymer are bonded using various modifiers or are modified.

Meanwhile, carbon black, silica, and the like are used as a reinforcing filler of tire treads. When silica is used as a reinforcing filler, low hysteresis loss and wet skid resistance are improved. However, silica with a hydrophilic surface has a lower affinity with rubber than that of carbon black with a hydrophobic surface, and thus has a problem such as poor dispersibility. Thus, it is necessary to use a separate silane coupling agent to enhance the dispersibility of silica and enable binding between silica and rubber.

Thus, studies on the introduction of functional groups with affinity or reactivity with silica to an end of rubber molecules have been conducted, but an effect thereof is insufficient.

DISCLOSURE

Technical Problem

The present invention has been made in view of the above problems, and it is one object of the present invention to provide a styrene-based compound useful for polymer modification.

It is another object of the present invention to provide a method of preparing the above-described styrene-based compound.

It is another object of the present invention to provide a modified polymer including a functional group derived from the above-described styrene-based compound.

It is another object of the present invention to provide a method of preparing the above-described modified polymer.

It is another object of the present invention to provide a rubber composition including the above-described modified polymer and a molded article manufactured therefrom.

Technical Solution

To address the above problems, the present invention provides a styrene-based compound represented by Formula 1 below:

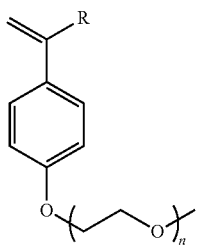

<Formula 1> in Formula 1 above, R may be a hydrogen atom or a $C_1$-$C_{20}$ hydrocarbon group, and n may be an integer of 1 to 11.

The present invention also provides a method of preparing a styrene-based compound, including reacting a compound represented by Formula 2 below with a compound represented by Formula 3 below:

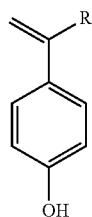

<Formula 2> in Formula 2, R may be a hydrogen atom or a $C_1$-$C_{20}$ hydrocarbon group,

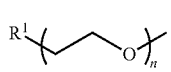

<Formula 3> in Formula 3, $R^1$ may be a halogen atom, and n may be an integer of 1 to 11.

The present invention also provides a modified polymer including a functional group derived from a modifier represented by Formula 1 above.

The present invention also provides a method of preparing a modified polymer, including polymerizing a monomer and the styrene-based compound represented by Formula 1 in the presence of an organometallic compound in a hydrocarbon solvent, wherein the monomer is an aromatic vinyl-based monomer or a combination of an aromatic vinyl-based monomer and a conjugated diene-based monomer.

The present invention also provides a rubber composition including the above-described modified polymer and a molded article manufactured using the same.

Advantageous Effects

The styrene-based compound represented by Formula 1 according to the present invention has an ethylene glycol group introduced thereto, and thus has high anionic reactivity and, accordingly, easily reacts with an active site of a polymer, whereby modification is easily performed.

In addition, a modified polymer according to the present invention includes a functional group derived from the styrene-based compound represented by Formula 1, for example, an ethylene glycol group, and thus has a strong affinity with a filler such as silica or the like.

In addition, the modified polymer according to the present invention includes a compound represented by Formula 4 at one end thereof, and thus has excellent interaction with a filler.

In addition, a method of preparing a modified polymer, according to the present invention, uses the styrene-based compound represented by Formula 1. At this time, the compound can act as a polar solvent, and thus may be easily bonded to an active site of a polymer, resulting in a reduction in the use of a polar solvent, whereby an economical effect can be obtained and a modified polymer with a high modification rate can be easily prepared.

Furthermore, a rubber composition according to the present invention includes the modified polymer with a strong affinity with a filler, and thus has excellent processability, and, consequently, molded articles (e.g., tires) manufactured using the rubber composition has excellent effects in terms of tensile strength, wear resistance, and wet skid resistance.

BEST MODE

Hereinafter, the present invention will be described in more detail with reference to the following examples and experimental examples. However, these examples and experimental examples are provided for illustrative purposes only and are not intended to limit the scope of the present invention.

Preparation Example 1: Preparation of 1-(2-methoxyethoxy)-4-vinylbenzene

1) Preparation of Hydroxystyrene 0.275 mol of sodium hydroxide was put into a 500 ml round-bottom flask, 60 ml of anhydrous ethanol was added thereto to dissolve the sodium hydroxide, and then 0.065 mol of acetoxystyrene was added to the flask, and the resulting solution was stirred at room temperature in a nitrogen atmosphere for 4 hours. Subsequently, 50 ml of distilled water and 30 ml of ethyl acetate were sequentially added to the resulting mixture to extract an organic layer, and the organic layer extraction process was repeated three times. The extracted organic layer was dried with anhydrous magnesium sulfate and filtered to remove any remaining moisture. Thereafter, the solvent was removed under reduced pressure to obtain 7.54 g (yield: 96%) of yellow solid hydroxystyrene. $^1$H nuclear magnetic resonance (NMR) spectroscopic data of the purified hydroxystyrene is as follows:

$^1$H-NMR (500 MHz, $CDCl_3$) δ 7.31-7.29 (d, J=9.5, 1H), δ 6.80-6.78 (d, J=8.5, Ar—H, 2H), δ 6.68-6.62 (q, J=9.5, 1H), δ 5.62-5.58 (d, J=17.5, 1H), δ 5.13-5.11 (d, J=11, 1H), δ 4.75 (s, 1H).

2) Preparation of 1-(2-methoxyethoxy)-4-vinylbenzene 0.058 mmol of hydroxystyrene was put into a 500 ml round-bottom flask, 50 ml of acetonitrile was added thereto to dissolve the hydroxystyrene, and then 0.071 mol of potassium t-butoxide was added dropwise to the flask, and the resulting solution was refluxed for 1 hour. Subsequently, 0.076 mol of 2-chloroethylmethylether was slowly added dropwise to the resulting mixture and then the resulting solution was refluxed in a nitrogen atmosphere for 6 hours to allow a reaction to occur therebetween. After the reaction was completed, the reaction product was neutralized with an aqueous hydrochloric acid solution, and then an organic layer was extracted with ethyl acetate/a saturated aqueous solution of a base, and the organic layer was dried with anhydrous magnesium sulfate and filtered to remove the remaining moisture. Thereafter, the solvent was removed under reduced pressure and, as a result, 9.9 g (95%) of a title compound represented by Formula (i) below was obtained as a pale brown liquid. $^1$H NMR spectroscopic data of the purified 1-(2-methoxyethoxy)-4-vinylbenzene (i) is as follows:

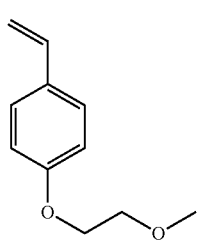

(i)

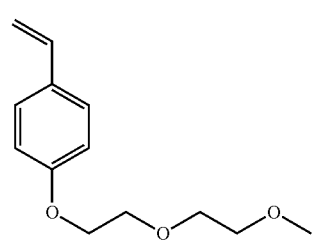

(ii)

¹H-NMR (500 MHz, CDCl₃) δ 7.33-7.31 (d, J=9, Ar—H, 2H), δ 6.88-6.86 (d, J=8.5, Ar—H, 2H), δ 6.67-6.61 (q, J=9.5, 1H), δ 5.61-5.57 (d, J=17.5, 1H), δ 5.12-5.10 (d, J=11, 1H), δ 4.10-4.08 (t, J=4.5, 2H), δ 3.73-3.71 (t, J=4.75, 2H), δ 3.43 (s, 3H).

Preparation Example 2: Preparation of 1-(2-(2-methoxyethoxy)ethoxy)-4-vinylbenzene 1) Preparation of Hydroxystyrene 0.275 mol of sodium hydroxide was put into a 500 ml round-bottom flask, 60 ml of anhydrous ethanol was added thereto to dissolve the sodium hydroxide, and then 0.065 mol of acetoxystyrene was added to the flask, and the resulting solution was stirred at room temperature in a nitrogen atmosphere for 4 hours. Subsequently, 50 ml of distilled water and 30 ml of ethyl acetate were sequentially added to the resulting mixture to extract an organic layer, and the organic layer extraction process was repeated three times. The extracted organic layer was dried with anhydrous magnesium sulfate and filtered to remove the remaining moisture. Thereafter, the solvent was removed under reduced pressure to obtain 7.54 g (yield: 96%) of yellow solid hydroxystyrene. ¹H NMR spectroscopic data of the purified hydroxystyrene is as follows.

¹H-NMR (500 MHz, CDCl₃) δ 7.31-7.29 (d, J=9.5, 1H), δ 6.80-6.78 (d, J=8.5, Ar—H, 2H), δ 6.68-6.62 (q, J=9.5, 1H), δ 5.62-5.58 (d, J=17.5, 1H), δ 5.13-5.11 (d, J=11, 1H), δ 4.75 (s, 1H).

2) Preparation of 1-(2-(2-methoxyethoxy)ethoxy)-4-vinylbenzene 0.058 mmol of hydroxystyrene was put into a 500 ml round-bottom flask, 50 ml of acetonitrile was added thereto to dissolve the hydroxystyrene, and then 0.071 mol of potassium t-butoxide was added dropwise to the flask, and the resulting solution was refluxed for 1 hour. Subsequently, 0.076 mol of 1-bromo-2-(2-methoxyethoxy)ethane was slowly added dropwise to the resultant and then refluxed in a nitrogen atmosphere for 6 hours to allow a reaction to occur therebetween. After the reaction was completed, the reaction product was neutralized with an aqueous hydrochloric acid solution, and then an organic layer was extracted with ethyl acetate/a saturated aqueous solution of a base, and the organic layer was dried with anhydrous magnesium sulfate and filtered to remove any remaining moisture. Thereafter, the solvent was removed under reduced pressure and, as a result, 10 g (96%) of a title compound represented by Formula (ii) below was obtained as a pale brown liquid. ¹H NMR spectroscopic data of the purified 1-(2-(2-methoxyethoxy)ethoxy)-4-vinylbenzene (ii) is as follows:

¹H-NMR (500 MHz, CDCl₃) δ 7.33-7.32 (d, J=8.5, Ar—H, 2H), δ 6.88-6.86 (d, J=8.5, Ar—H, 2H), δ 6.68-6.62 (q, J=9.5, 1H), δ 5.62-5.58 (d, J=17.5, 1H), δ 5.13-5.10 (d, J=11, 1H), δ 4.15-4.13 (t, J=5, 2H), δ 3.87-3.85 (t, J=5, 2H), δ 3.73-3.71 (t, J=4.7, 2H), δ 3.59-3.57 (t, J=4.5, 2H), δ 3.39 (s, 3H).

Example 1: Preparation of Modified Styrene Polymer 28.8 mmol of styrene and 1.4 mmol of the styrene-based compound prepared according to Preparation Example 2 were put into a 100 ml Schlenk flask, 30 ml of anhydrous n-hexane was added thereto, and then the temperature inside the flask was raised to 40° C. When the temperature inside the reactor reached 40° C., 0.25 ml (0.63 mmol in hexane) of a 2.5 M n-butyl lithium hexane solution was added to the reactor to allow an adiabatic heating reaction to occur. After about 20 minutes, the polymerization reaction was terminated using methanol to complete the preparation of a modified styrene polymer.

Example 2: Preparation of Modified Styrene Polymer

A modified styrene polymer was prepared in the same manner as in Example 1, except that 2.9 mmol of the styrene-based compound of Preparation Example 2 was added.

Example 3: Preparation of Modified Styrene Polymer

A modified styrene polymer was prepared in the same manner as in Example 1, except that 4.3 mmol of the styrene-based compound of Preparation Example 2 was added.

Example 4: Preparation of Modified Styrene-Butadiene Copolymer 4.2 g of styrene, 7.5 g of 1,3-butadiene, and 0.045 g of the styrene-based compound of Preparation Example 2 were put into a 2 L glass reactor, 50 ml of anhydrous n-hexane was added thereto, and then the temperature inside the reactor was raised to 40° C. When the temperature inside the reactor reached 40° C., 0.20 ml (0.5 mmol in hexane) of a 2.5 M n-butyl lithium hexane solution was added to the reactor to allow an adiabatic heating reaction to occur. After about 30 minutes, the polymerization reaction was terminated using methanol to complete the preparation of a modified styrene-butadiene copolymer.

Example 5: Preparation of Modified Styrene-Butadiene Copolymer

A modified styrene-butadiene copolymer was prepared in the same manner as in Example 4, except that 0.09 g of the styrene-based compound of Preparation Example 2 was added.

Example 6: Preparation of Modified Styrene-Butadiene Copolymer

A modified styrene-butadiene copolymer was prepared in the same manner as in Example 4, except that 0.18 g of the styrene-based compound of Preparation Example 2 was added.

Example 7: Preparation (Scale-Up) of Modified Styrene-Butadiene Copolymer 270 g of styrene, 730 g of 1,3-butadiene, and 4 g of the styrene-based compound of Preparation Example 1 were put into a 20 L autoclave reactor, 5 kg of anhydrous n-hexane and 0.75 g of 2,2-bis(2-oxoranyl)propane (DTP) as a polar additive were added thereto, and the temperature inside the reactor was raised to 40° C. When the temperature inside the reactor reached 40° C., 34 g (2.62 wt % in hexane, 33% activation) of n-butyl lithium was added to the reactor to allow an adiabatic heating reaction to occur. After 35 minutes, the polymerization reaction was terminated using ethanol to complete the preparation of a modified styrene-butadiene copolymer.

Example 8: Preparation (Scale-Up) of Modified Styrene-Butadiene Copolymer

A modified styrene-butadiene copolymer was prepared in the same manner as in Example 7, except that the styrene-based compound prepared according to Preparation Example 2 was used instead of the styrene-based compound of Preparation Example 1.

Comparative Example 1: Preparation of Styrene Polymer

A styrene polymer was prepared in the same manner as in Example 1, except that the styrene-based compound of Preparation Example 2 was not used.

Comparative Example 2: Preparation of Styrene-Butadiene Copolymer

A styrene-butadiene copolymer was prepared in the same manner as in Example 4, except that the styrene-based compound of Preparation Example 2 was not used.

Comparative Example 3: Preparation of Styrene-Butadiene Copolymer

A styrene-butadiene copolymer was prepared in the same manner as in Example 4, except that that the styrene-based compound of Preparation Example 2 was not used, and 0.045 g of ditetrahydrofurylpropane was further used.

Comparative Example 4: Preparation (Scale-Up) of Styrene-Butadiene Copolymer A styrene-butadiene copolymer was prepared in the same manner as in Example 7, except that the styrene-based compound of Preparation Example 1 was not used.

Experimental Example 1

To compare and analyze physical properties of each of the polymers prepared according to Examples 1 to 8 and Comparative Examples 1 to 4, component analysis, a weight average molecular weight (Mw), a number average molecular weight (Mn), a polydispersity index (PDI) (Mw/Mn), a maximum peak molecular weight (Mp), and a Z-average molecular weight (Mz) of each polymer were measured. The results thereof are shown below in Tables 1 to 3.

1) Component Analysis
For the component analysis, contents of a styrene monomer (St) and a vinyl were measured by NMR.

2) Gel Permeation Chromatography (GPC) Analysis
Mw, Mn, and Mp were measured by GPC analysis at a temperature of 40° C., and PDI (Mw/Mn) was calculated using the measured Mw and Mn. In particular, the GPC was performed using, as a column, a combination of two PLgel Olexis columns (manufactured by Polymer Laboratories) and one PLgel mixed-C column (manufactured by Polymer Laboratories), all newly replaced columns were mixed bed-type columns, and polystyrene (PS) was used as a GPC standard material for the calculation of molecular weights.

TABLE 1

|  | Mn (g/mol) | Mw (g/mol) | Mp (g/mol) | PDI (Mw/Mn) |
|---|---|---|---|---|
| Example 1 | 5,886 | 8,430 | 7,876 | 1.43 |
| Example 2 | 7,269 | 10,754 | 9,375 | 1.47 |
| Example 3 | 7,079 | 11,248 | 8,470 | 1.58 |
| Comparative Example 1 | 5,976 | 6,907 | 7,253 | 1.15 |

TABLE 2

|  | BD:St:vinyl (molar ratio) | Mn (g/mol) | Mw (g/mol) | Mp (g/mol) | PDI (Mw/Mn) |
|---|---|---|---|---|---|
| Example 4 | 24:34:42 | 49,260 | 57,531 | 53,867 | 1.16 |
| Example 5 | 22:38:40 | 59,012 | 75,913 | 67,183 | 1.28 |
| Example 6 | 19:39:42 | 69,103 | 137,291 | 128,542 | 1.98 |
| Comparative Example 2 | 85:6:9 | 11,278 | 13,507 | 12,314 | 1.19 |
| Comparative Example 3 | 21:36:43 | 52,305 | 58,293 | 54,811 | 1.11 |

* BD: 1,3-butadiene-derived unit
* St: Styrene-derived unit
* vinyl: vinyl component

TABLE 3

|  | BD:St:vinyl (molar ratio) | Mn (g/mol) | Mw (g/mol) | Mp (g/mol) | PDI (Mw/Mn) |
|---|---|---|---|---|---|
| Example 7 | 23.6:29.1:47.3 | 513,230 | 642,022 | 611,461 | 1.25 |
| Example 8 | 21.6:30.8:47.6 | 433,836 | 613,646 | 685,777 | 1.41 |
| Comparative Example 4 | 28.3:27.3:44.4 | 321,920 | 340,025 | 342,553 | 1.05 |

* BD: 1,3-butadiene-derived unit
* St: Styrene-derived unit
* vinyl: vinyl component As shown above in Tables 1 to 3, it was confirmed that the modified polymers prepared according to Examples 1 to 8 using each of the substituted styrene-based compound of Preparation Example 1 and 2 according to an embodiment of the present invention had higher molecular weights than those of the polymers prepared according to Comparative Examples 1 to 4.

In particular, as shown in Table 1, the modified styrene polymers prepared according to Examples 1 to 3 using the substituted styrene-based compound of Preparation Example 2 had higher molecular weights than that of the styrene polymer of Comparative Example 1 which did not use the substituted styrene-based compound, and, as the amount of the substituted styrene-based compound used increased (Example 1<Example 2<Example 3), higher molecular weights were exhibited. This indicates that the styrene monomer used in polymerization of a polymer and the substituted styrene-based compound were easily copolymerized. The results were also seen in NMR measurement results. In particular, as a result of NMR analysis (500 MHz, CDCl3), vinyl peaks (δ 5.62-5.58, 5.13-5.10) were not observed in the prepared modified styrene polymers, which indicates that the styrene-based monomer and the substituted styrene-based compound that did not participate in the polymerization reaction were completely removed.

In addition, as shown in Table 2, the modified styrene-butadiene copolymers prepared according to Examples 4 to 6 using the substituted styrene-based compound of Preparation Example 2 had higher molecular weights than those of the styrene-butadiene copolymers of Comparative Examples 2 and 3 which did not use the substituted styrene-based compound, and, as the amount of the substituted styrene-based compound used increased (Example 4<Example 5<Example 6), higher molecular weights were exhibited. In addition, as a result of comparing the modified styrene-butadiene copolymer of Example 4 with the styrene-butadiene copolymer prepared according to Comparative Example 3, which used a polar additive, the modified styrene-butadiene copolymer of Example 4 exhibited similar contents of styrene and vinyl (result of 1,2-addition polymerization of butadiene) and a similar microstructure to those of the styrene-butadiene copolymer prepared according to Comparative Example 3, which used a polar additive, even without the use of a polar additive. The results indicate that polarity was exhibited due to the presence of an ethylene glycol group in the substituted styrene-based compound and, accordingly, a similar effect to that obtained using a polar additive may be obtained.

In addition, as shown in Table 3, from the results of scale-up polymerization, it was confirmed that the modified styrene-butadiene copolymers of Examples 7 and 8 according to the present invention exhibited higher molecular weights and larger contents of styrene and vinyl in a microstructure thereof than those of the styrene-butadiene copolymer of Comparative Example 4.

MODE OF THE INVENTION

Hereinafter, the present invention will be described in more detail to aid in understanding of the present invention.

The terms or words used in the present specification and claims are not to be construed as being limited to ordinary or dictionary meanings and should be construed as having meanings and concepts consistent with the spirit of the present invention based on a principle that an inventor can appropriately define concepts of terms to explain the invention in the best way.

The present invention provides a styrene-based compound useful for modifying a polymer. According to an embodiment of the present invention, the styrene-based compound may be represented by Formula 1 below:

<Formula 1> in Formula 1, R may be a hydrogen atom or a $C_1$-$C_{20}$ hydrocarbon group, and n may be an integer of 1 to 11.

The styrene-based compound represented by Formula 1 may be a modified monomer for modifying a polymer, and may provide a functional group capable of changing physical properties of a modified polymer modified using the styrene-based compound.

In particular, the substituted styrene-based compound represented by Formula 1 is used as a modified monomer, and thus may be bonded to a main chain of a polymer and, accordingly, the functional group may be introduced into the polymer with a high yield. In addition, the substituted styrene-based compound may include a functional group having affinity with an inorganic filler to enhance wear resistance and processability of a rubber composition via an interaction with the inorganic filler. In particular, the functional group having affinity with an inorganic filler may be an ethylene glycol group, and may enhance the wear resistance and processability of a polymer via a condensation reaction with a functional group on a surface of an inorganic filler, e.g., in a case in which the inorganic filler is silica, a silanol group on a surface of the silica, after being introduced into the polymer. In addition, the substituted styrene-based compound includes an ethylene glycol group, and thus may also act as a polar solvent used in polymerization of a polymer and reduce the use of a polar solvent.

In particular, in Formula 1 above, R may be a hydrogen atom, a $C_1$-$C_{20}$ alkyl group, a $C_3$-$C_{20}$ cycloalkyl group, a $C_6$-$C_{20}$ aryl group, a $C_7$-$C_{20}$ arylalkyl group, a $C_1$-$C_{20}$ alkoxy group, a $C_2$-$C_{20}$ alkoxyalkyl group, or a $C_7$-$C_{20}$ phenoxyalkyl group.

More particularly, in Formula 1 above, R may be a hydrogen atom, and n may be an integer of 1 to 11.

The styrene-based compound according to the present invention is used as a monomer for modifying a polymer, and thus may impart excellent viscoelasticity, tensile properties, and processability to the polymer.

In this regard, the polymer may be a polymer including an aromatic vinyl-based monomer-derived unit. In addition, the polymer may be a copolymer including a conjugated diene-based monomer-derived unit and an aromatic vinyl-based monomer-derived unit. That is, according to an embodiment of the present invention, the polymer may be a homopolymer including an aromatic vinyl-based monomer-derived unit, or a copolymer including a conjugated diene-based monomer-derived unit and an aromatic vinyl-based monomer-based unit.

The term "derived unit" as used herein may indicate a component or structure derived from a material or the material itself.

The present invention also provides a method of preparing a styrene-based compound.

The method of preparing a styrene-based compound, according to an embodiment of the present invention, may include reacting a compound represented by Formula 2 below with a compound represented by Formula 3 below:

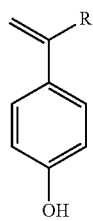

<Formula 2> in Formula 2, R may be a hydrogen atom or a $C_1$-$C_{20}$ hydrocarbon group,

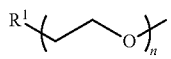

<Formula 3> in Formula 3, $R^1$ may be a halogen atom, and n may be an integer of 1 to 11.

In particular, the compound represented by Formula 2 may be a hydroxy styrene (o-, m-, or p-hydroxyl styrene), and the compound represented by Formula 3 may be 2-chloroethylmethylether or 1-bromo-2-(2-methoxyethoxy)ethane.

The compounds represented by Formulae 2 and 3 may be used in a stoichiometric amount. In particular, the amount of the compound represented by Formula 3 may range from 1.1 mol to 2.5 mol with respect to 1 mol of the compound represented by Formula 2.

In addition, the reaction between the compounds represented by Formulae 2 and 3 may be performed in an organic solvent. The organic solvent is not particularly limited but may be, for example, tetrahydrofuran or acetonitrile.

In addition, the reaction between the compounds represented by Formulae 2 and 3 may be performed in an inert gas atmosphere. In this regard, nitrogen, argon, or the like may be used as the inert gas.

In addition, the reaction between the compounds represented by Formulae 2 and 3 may be performed at a temperature ranging from 70° C. to 90° C. When the reaction temperature is outside the above range, e.g., too low, the reaction does not proceed and the reactants may be present in a mixed state.

Meanwhile, the compound represented by Formula 2 may be prepared through Reaction Scheme 1 below:

<Reaction Scheme 1>

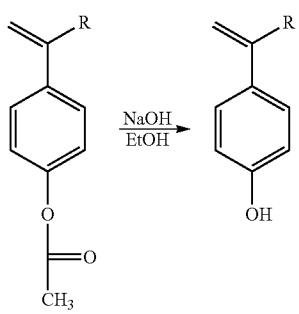

in Reaction Scheme 1, R may be the same as the above-described R.

In particular, according to an embodiment of the present invention, the compound represented by Formula 2 may be prepared by substituting an acetate group of a compound represented by Formula (i) in Reaction Scheme 1 with a hydroxyl group. At this time, the substituting process may be performed in an inert gas atmosphere, and the inert gas may be the same as that described above.

The present invention also provides a modified polymer including a functional group derived from a styrene-based compound represented by Formula 1 below:

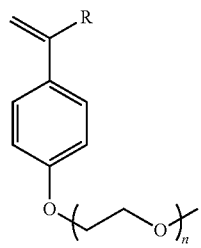

<Formula 1> in Formula 1, R may be a hydrogen atom or a $C_1$-$C_{20}$ hydrocarbon group, and n may be an integer of 1 to 11.

The modified polymer according to an embodiment of the present invention may be prepared using the following preparation method, and the modified polymer may include the functional group derived from a styrene-based compound represented by Formula 1 above at a main chain thereof, and thus may have enhanced physical properties.

A detailed description of the styrene-based compound represented by Formula 1 has already been provided.

In another embodiment, the modified polymer may include, at one end thereof, a functional group derived from a modifier.

The modifier may be, for example, a compound represented by Formula 4 below:

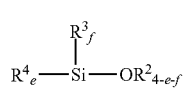

<Formula 4> in Formula 4, each of $R^2$ and $R^3$ may independently be a $C_1$-$C_{20}$ alkyl group, $R^4$ may be one selected from the group consisting of functional groups represented by Formulae 5 to 8 below, e may be 1 or 2, and f may be an integer selected from 0, 1, and 2, wherein e and f may not simultaneously be 2,

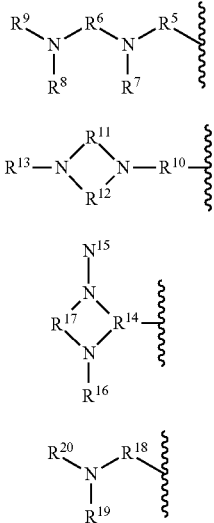

<Formula 5>
<Formula 6>
<Formula 7>
<Formula 8> in Formulae 5 to 8, each of $R^5$, $R^6$, $R^{10}$, $R^{11}$, $R^{12}$, $R^{17}$, and $R^{18}$ may independently be a linear or branched $C_1$-$C_{20}$ alkylene group, each of $R^7$, $R^8$, $R^9$, $R^{13}$, $R^{15}$, $R^{16}$, $R^{19}$, and $R^{20}$ may independently be a $C_1$-$C_{20}$ alkyl group or a $C_1$-$C_{20}$ alkylsilyl group, and $R^{14}$ may be a trivalent $C_1$-$C_{20}$ hydrocarbon group.

In particular, in Formula 4 above, each of $R^2$ and $R^3$ may independently be a $C_1$-$C_{10}$ alkyl group, $R^4$ may be one selected from the group consisting of functional groups represented by Formulae 5 to 8 above, e may be 1 or 2, and f may be an integer selected from 0, 1, and 2, wherein e and f may not simultaneously be 2, and in Formulae 5 to 8 above, each of $R^5$, $R^6$, $R^{10}$, $R^{11}$, $R^{12}$, $R^{17}$, and $R^{18}$ may independently be a linear $C_1$-$C_{10}$ alkylene group, each of $R^7$, $R^8$, $R^9$, $R^{13}$, $R^{15}$, $R^{16}$, $R^{19}$ and $R^{20}$ may independently be a $C_1$-$C_{10}$ alkyl group or a $C_1$-$C_{10}$ alkylsilyl group, and $R^{14}$ may be a trivalent $C_1$-$C_{10}$ hydrocarbon group.

More particularly, the compound represented by Formula 4 may be one selected from the group consisting of compounds represented by Formulae 9 to 13 below:

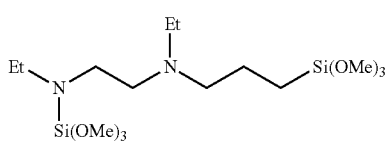

<Formula 9>

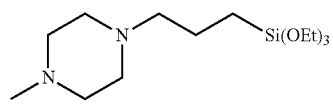

<Formula 10>

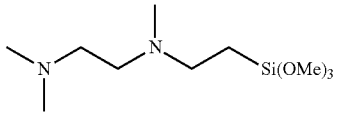

<Formula 11>

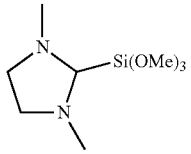

<Formula 12>

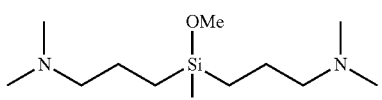

<Formula 13> in Formulae 9 to 13, Me is a methyl group and Et is an ethyl group.

In this case, the modified polymer includes, at one end thereof, the compound represented by Formula 4 as a functional group derived from a modifier, and thus exhibits excellent interaction with a filler, whereby excellent processability, high tensile strength, and excellent viscoelastic properties may be obtained.

Meanwhile, the modified polymer may be a homopolymer or a copolymer. When the modified polymer is a homopolymer, the modified polymer may be a modified polymer including a unit derived from an aromatic vinyl-based monomer, and when the modified polymer is a copolymer, the modified polymer may include a unit derived from a conjugated diene-based monomer and a unit derived from an aromatic vinyl-based monomer. In addition, when the modified polymer is a copolymer, the copolymer may be a random copolymer.

The term "random copolymer" as used herein may refer to a copolymer consisting of randomly arranged constituent units.

The conjugated diene-based monomer is not particularly limited, but may be, for example, one or more selected from the group consisting of 1,3-butadiene, 2,3-dimethyl-1,3-butadiene, piperylene, 3-butyl-1,3-octadiene, isoprene, and 2-phenyl-1,3-butadiene.

When the modified polymer is a copolymer, the modified polymer may include the unit derived from a conjugated diene-based monomer in an amount of 60 wt % or more, particularly, 60 wt % to 90 wt %, and more particularly, 60 wt % to 85 wt %.

The aromatic vinyl-based monomer is not particularly limited, but may be, for example, one or more selected from the group consisting of styrene, α-methyl styrene, 3-methyl styrene, 4-methyl styrene, 4-propylstyrene, 1-vinylnaphthalene, 4-cyclohexylstyrene, 4-(p-methylphenyl)styrene, and 1-vinyl-5-hexylnaphthalene.

When the modified polymer is a copolymer, the modified polymer may include the unit derived from an aromatic vinyl-based monomer in an amount of 40 wt % or more, particularly, 10 wt % to 40 wt %, and more particularly, 15 wt % to 40 wt %.

In addition, the modified polymer may have a molecular weight distribution (Mw/Mn) of 1.0 to 3.0, particularly, 1.0 to 2.5, and more particularly, 1.0 to 2.0. When the molecular weight distribution of the modified polymer is within the above range, a rubber composition including the same may have enhanced processability and a resulting molded article manufactured therefrom may exhibit enhanced mechanical characteristics, enhanced fuel efficiency characteristics, and enhanced wear resistance.

The modified polymer may have a vinyl content of 5 wt % or more, particularly, 10 wt % or more, and more particularly, 15 wt % to 70 wt %. When the vinyl content of the modified polymer is within the above range, a glass transition temperature may be appropriately adjusted such that the modified polymer may satisfy physical properties required for tires, such as driving resistance and braking force and provides an effect of reducing fuel consumption when applied to a tire.

In this regard, the vinyl content refers to the content of a not 1,4-added but 1,2-added conjugated diene-based monomer with respect to 100 wt % of a polymer consisting of a vinyl group-containing monomer and an aromatic vinyl-based monomer.

The present invention also provides a method of preparing a modified polymer including a functional group derived from a styrene-based compound represented by Formula 1 below.

The preparation method according to an embodiment of the present invention includes polymerizing a monomer and the substituted styrene-based compound represented by Formula 1, in a hydrocarbon solvent including an organometallic compound, wherein the monomer is an aromatic vinyl-based monomer or a combination of an aromatic vinyl-based monomer and a conjugated diene-based monomer.

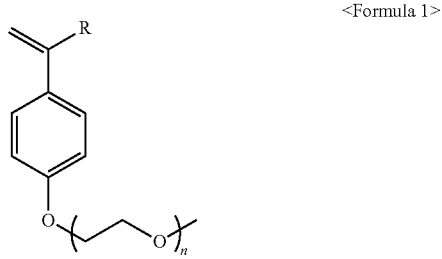

<Formula 1>

In Formula 1 above, R may be a hydrogen atom or a $C_1$-$C_{20}$ hydrocarbon group, and n may be an integer of 1 to 11.

In another embodiment, the method of preparing a modified polymer, according to the present invention, may include reacting a terminal-active polymer prepared by the polymerizing process with a modifier.

The modifier may be a compound represented by Formula 4 below:

<Formula 4> in Formula 4, substituents have already been defined above.

The polymerizing is a process of preparing a modified polymer with a functional group derived from the substituted styrene-based compound represented by Formula 1, introduced into a main chain thereof, and may be performed by polymerizing a monomer and the styrene-based compound represented by Formula 1 in the presence of an organometallic compound in a hydrocarbon solvent. In this regard, as described above, the monomer may be an aromatic vinyl-based monomer or a combination of an aromatic vinyl-based monomer and a conjugated diene-based monomer.

Particular types of the conjugated diene-based monomer and the aromatic vinyl-based monomer may be the same as those described above, and the amount of each monomer used may be appropriately adjusted within the above ranges within which the amounts of the conjugated diene-based monomer-derived unit and the aromatic vinyl-based monomer-based unit, in the modified polymer, are adjusted.

The hydrocarbon solvent is not particularly limited, and may be, for example, one or more selected from the group consisting of n-pentane, n-hexane, n-heptane, isooctane, cyclohexane, toluene, benzene, and xylene.

The organometallic compound may be an organo-alkali-metallic compound, for example, one or more selected from the group consisting of an organolithium compound, an organosodium compound, an organopotassium compound, an organorubidium compound, and an organocesium compound.

In particular, the organometallic compound may be one or more selected from the group consisting of methyllithium, ethyllithium, propyllithium, n-butyllithium, s-butyllithium, t-butyllithium, hexyllithium, n-decyllithium, t-octyllithium, phenyllithium, 1-naphthyllithium, n-eicosyllithium, 4-butylphenyllithium, 4-tolyllithium, cyclohexyllithium, 3,5-di-n-heptylcyclohexyllithium, 4-cyclopentyllithium, naphthylsodium, naphthylpotassium, lithium alkoxide, sodium alkoxide, potassium alkoxide, lithium sulfonate, sodium sulfonate, potassium sulfonate, lithium amide, sodium amide, potassium amide, and lithium isopropylamide.

The organometallic compound may be used in an amount of 0.01 mmol to 10 mmol based on the total 100 g of the monomer. In particular, the amount of the organometallic compound may range from 0.05 mmol to 5 mmol, particularly, 0.1 mmol to 2 mmol, and more particularly, 0.1 mmol to 1 mmol, based on the total 100 g of the monomer.

The styrene-based compound represented by Formula 1 may be the same as that described above. The substituted styrene-based compound represented by Formula 1 may be used in an amount of 0.1 wt % to 15 wt % with respect to the monomer. In particular, the amount of the styrene-based compound represented by Formula 1 may range from 0.5 wt % to 5 wt % with respect to the monomer. More particularly, the styrene-based compound may be used in the above amount ratio relative to the aromatic vinyl-based monomer from among the monomers. When the styrene-based compound is used within the above amount ratio range, modification with optimum performance may be performed, and, consequently, a polymer having a high modification rate may be obtained.

The polymerizing may be performed by further including a polar additive according to need, and the polar additive may be added in an amount of 0.001 g to 5 g, particularly, 0.001 g to 1 g, and more particularly, 0.005 g to 0.1 g, based on the total 100 g of the monomer.

In addition, the polar additive may be added in an amount of 0.1 mmol to 10 mmol, particularly, 0.2 mmol to 5 mmol, and more particularly, 0.5 mmol to 3 mmol, based on the total 1 mmol of the organometallic compound.

The polar additive may be a salt, an ether, an amine, or a mixture thereof, and, in particular, may be one or more selected from the group consisting of tetrahydrofuran, ditetrahydrofurylpropane, diethylether, cycloamylether, dipropylether, ethylenedimethylether, diethylglycol, dimethylether, tert-butoxyethoxyethane, bis(3-dimethylaminoethyl)ether, (dimethylaminoethyl)ethylether, trimethylamine, triethylamine, tripropylamine, and tetramethylethylenediamine.

More particularly, the polar additive may be ditetrahydropropylpropane, trimethylamine, or tetramethylethylenediamine.

In the preparation method according to an embodiment of the present invention, a polar additive is used, and thus, when the conjugated diene-based monomer and the aromatic vinyl-based monomer are copolymerized, a difference between reaction rates thereof may be compensated for such that easy formation of a random copolymer is induced.

The polymerizing process may be anionic polymerization, and in particular, may be living anionic polymerization in which an active site is obtained through a growth reaction by anions.

In addition, the polymerizing process may be heating polymerization (adiabatic heating polymerization), isothermal polymerization, or room-temperature polymerization (adiabatic polymerization).

In this regard, the room-temperature polymerization may refer to a polymerization method including performing polymerization with a reaction heat itself without arbitrarily applying heat after the organometallic compound is added, the heating polymerization may refer to a polymerization method in which the organometallic compound is added and then heat is applied to increase the reaction temperature, and the isothermal polymerization may refer to a polymerization method in which the organometallic compound is added and then heat is applied thereto to increase the temperature or take heat away therefrom to constantly maintain the temperature of the polymerized product.

The polymerizing process may be performed at a temperature ranging from −20° C. to 200° C., in particular, 0° C. to 150° C., and more particularly, 10° C. to 120° C.

In addition, the method of preparing a modified polymer, according to an embodiment of the present invention, may be performed by a batch-type polymerization method or a continuous-type polymerization method including one or more reactors.

The preparation method according to an embodiment of the present invention may further include, after the polymerizing process or a modifying process, one or more processes selected from recovering and drying a solvent and unreacted monomers according to need.

The present invention also provides a rubber composition including the above-described modified polymer.

The rubber composition according to an embodiment of the present invention may include the modified polymer in an amount of 10 wt % or more, in particular, 10 wt % to 100 wt %, and more particularly, 20 wt % to 90 wt %. When the amount of the modified polymer is less than 10 wt %, consequently, a molded article manufactured using the rubber composition may have an insignificant improvement effect in terms of wear resistance, crack resistance, and the like of tires.

In addition, the rubber composition may further include other rubber components as necessary, in addition to the modified polymer, and the rubber components may be included in an amount of 90 wt % or less with respect to the total weight of the rubber composition. In particular, the other rubber components may be included in an amount of 1 part by weight to 900 parts by weight with respect to 100 parts by weight of the modified polymer.

The rubber component may be a natural rubber or synthetic rubber, and examples of such rubber components include: a natural rubber (NR) including cis-1,4-polyisoprene; a modified NR obtained by modifying or purifying such general NR, such as epoxidized NR (ENR), deproteinized NR (DPNR), hydrogenated NR, and the like; and a synthetic rubber such as a styrene-butadiene rubber (SBR) copolymer, polybutadiene rubber (BR), polyisoprene rubber (IR), butyl rubber (IIR), an ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acryl rubber, urethane rubber, silicone rubber, epichlorohydrin rubber, butyl rubber, halogenated butyl rubber, and the like. Any one selected from the above-listed materials or a mixture of two or more of these materials may be used.

In addition, the rubber composition may include a filler in an amount of 0.1 parts by weight to 200 parts by weight, and in particular, 10 parts by weight to 120 parts by weight, with respect to 100 parts by weight of the modified polymer. The filler may be a silica-based filler, and the silica-based filler is not particularly limited, but may be, for example, wet silica (hydrous silicic acid), dry silica (anhydrous silicic acid), calcium silicate, aluminum silicate, colloidal silica, or the like. More particularly, the filler may be wet silica having both the most significant improvement effect on fracture properties and the most significant wet gripping properties. In addition, the rubber composition according to an embodiment of the present invention may further include a carbon black-based filler as necessary.

Meanwhile, when silica is used as the filler, a silane coupling agent may be used therewith to improve reinforcing properties and low exothermicity. In particular, the silane coupling agent may be bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl)tetrasulfide, 3-mercaptopropyldimethoxymethylsilane, dimethoxymethylsilylpropyl-N,N-dimethylthiocarbamoyltetrasulfide, dimethoxymethylsilylpropylbenzothiazolyltetrasulfide, or the like, and any one selected from the above-listed material or a mixture of two or more of these materials may be used. More particularly, in consideration of the effect of improving reinforcement properties, the silane coupling agent may be bis(3-triethoxysilylpropyl)polysulfide or 3-trimethoxysilylpropylbenzothiazyltetrasulfide.

In addition, since the rubber composition according to an embodiment of the present invention uses the modified polymer in which a functional group with high affinity with silica is introduced into an active site thereof, as a rubber component, the amount of the silane coupling agent to be mixed therewith may be decreased as compared to a general case. In particular, the silane coupling agent may be used in an amount of 1 part by weight to 20 parts by weight with respect to 100 parts by weight of silica. When the amount of the silane coupling agent is within the above range, an effect as a coupling agent may be sufficiently achieved and gelation of the rubber component may be prevented. More particularly, the silane coupling agent may be used in an amount of 5 parts by weight to 15 parts by weight with respect to 100 parts by weight of silica.

In addition, the rubber composition according to an embodiment of the present invention may be sulfur-cross-linkable, and thus may further include a vulcanizing agent.

The vulcanizing agent may be, in particular, sulfur powder, and may be included in an amount of 0.1 parts by weight to 10 parts by weight with respect to 100 parts by weight of the rubber component. When the amount of the vulcanizing agent is within the above range, elastic modulus and strength needed for a vulcanized rubber composition may be secured and high fuel efficiency may also be obtained.

The rubber composition according to an embodiment of the present invention may further include a variety of additives commonly used in the rubber industry, in particular, a vulcanization accelerator, process oil, a plasticizer, an antiaging agent, a scorch inhibitor, zinc white, stearic acid, thermosetting resin, thermoplastic resin, or the like, in addition to the above-listed components.

The vulcanization accelerator is not particularly limited, and in particular, may be a thiazol-based compound such as 2-mercaptobenzothiazol (M), dibenzothiazyldisulfide (DM), N-cyclohexyl-2-benzothiazylsulfeneamide (CZ), or the like, or a guanidine-based compound such as diphenylguanidine (DPG) or the like. The vulcanization accelerator may be included in an amount of 0.1 parts by weight to 5 parts by weight with respect to 100 parts by weight of the rubber component.

In addition, the process oil acts as a softener in the rubber composition, and in particular, may be a paraffin-based compound, a naphthene-based compound, or an aromatic compound. More particularly, an aromatic process oil may be used in consideration of tensile strength and wear resistance, and a naphthene- or paraffin-based process oil may be used in consideration of hysteresis loss and low-temperature properties. The process oil may be included in an amount of 100 parts by weight or less with respect to 100 parts by weight of the rubber component. When the amount of the process oil is within the above range, an effect of preventing a decrease in tensile strength and low exothermicity (fuel efficiency) of the vulcanized rubber is obtained.

In addition, the antiaging agent may be, in particular, N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, a high-temperature condensed product of diphenylamine and acetone, or the like. The antiaging agent may be used in an amount of 0.1 parts by weight to 6 parts by weight with respect to 100 parts by weight of the rubber component.

The rubber composition according to an embodiment of the present invention may be obtained by kneading using a kneader such as a Banbury mixer, a roll, an internal mixer, or the like according to the mixing formulation, and a rubber composition with excellent low exothermicity and high wear resistance may be obtained by a vulcanizing process after molding processing.

Accordingly, the rubber composition may be usefully used in the manufacture of tire components such as tire treads, under treads, sidewalls, carcass-coated rubber, belt-coated rubber, bead fillers, chasers, bead-coated rubber, and the like, or in the manufacture of rubber products for various industries such as anti-vibration rubber, belt conveyors, hoses, and the like.

Furthermore, the present invention provides a molded article manufactured using the above-described rubber composition. The molded article may include tires or tire treads.

The invention claimed is:

1. A modified polymer comprising a repeating unit derived from a styrene-based compound represented by Formula 1 below, a unit derived from a conjugated diene-based monomer and a unit derived from an aromatic vinyl-based monomer, the modified polymer has a molecular weight distribution (Mw/Mn) of 1.0 to 2.0:

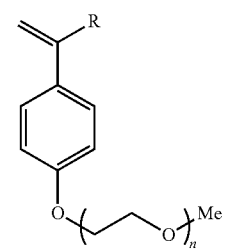

<Formula 1> wherein, in Formula 1, R is a hydrogen atom or a $C_1$-$C_{20}$ hydrocarbon group, and n is an integer of 1 to 11.

2. The modified polymer of claim 1, wherein the modified polymer comprises a functional group derived from a modifier at one end thereof, wherein the modifier is a compound represented by Formula 4 below:

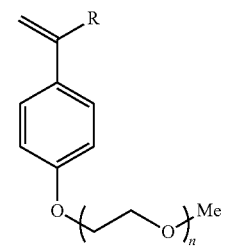

<Formula 1> in Formula 1, R is a hydrogen atom or a $C_1$-$C_{20}$ hydrocarbon group, and n is an integer of 1 to 11,

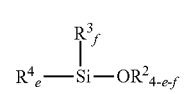

<Formula 4>

$$R^4{}_e\text{---}Si\text{---}OR^2{}_{4-e-f}$$
with $R^3{}_f$ above Si in Formula 4, each of $R^2$ and $R^3$ is independently a $C_1$-$C_{20}$ alkyl group, $R^4$ is one selected from the group consisting of functional groups represented by Formulae 5 to 8 below, e is 1 or 2, and f is an integer selected from 0, 1, and 2, wherein e and f are not simultaneously 2,

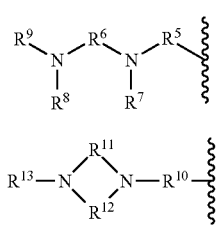

<Formula 5>

<Formula 6>

<Formula 7>

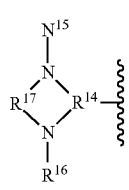

<Formula 8>

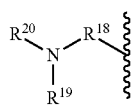

in Formulae 5 to 8, each of $R^5$, $R^6$, $R_{10}$, $R^{11}$, $R^{12}$, $R^{17}$, and $R^{18}$ is independently a linear or branched $C_1$-$C_{20}$ alkylene group, each of $R^7$, $R^8$, $R^9$, $R^{13}$, $R^{15}$, $R^{16}$, $R^{19}$, and $R^{20}$ is independently a $C_1$-$C_{20}$ alkyl group or a $C_1$-$C_{20}$ alkylsilyl group, and $R^{14}$ is a trivalent $C_1$-$C_{20}$ hydrocarbon group.

3. The modified polymer of claim 1, wherein the modified polymer comprises the unit derived from an aromatic vinyl-based monomer in an amount of 10 wt% or more.

4. The modified polymer of claim 1, wherein the modified polymer has a vinyl content of 5 wt% or more.

* * * * *